United States Patent [19]

Shim et al.

[11] Patent Number: 4,634,771

[45] Date of Patent: Jan. 6, 1987

[54] METHOD FOR CONVERTING CARBOXYLIC ACID GROUPS TO TRICHLOROMETHYL GROUPS

[75] Inventors: Kyung S. Shim, Irvington, N.Y.; Arthur D. F. Toy, Stamford, Conn.; James B. Heather, Hercules, Calif.

[73] Assignee: Stauffer Chemical Company, Westport, Conn.

[21] Appl. No.: 759,003

[22] Filed: Jul. 25, 1985

[51] Int. Cl.$^4$ .................. C07D 401/00; C07D 211/72; C07D 211/84; C07D 213/72

[52] U.S. Cl. .................................... 546/286; 546/346; 546/345; 546/297; 546/302; 570/185; 558/411; 568/630; 568/635; 568/716; 568/936; 568/927

[58] Field of Search ............... 546/346, 345, 286, 297, 546/302; 570/185; 558/411; 568/630, 635, 716, 936, 927

[56] References Cited

U.S. PATENT DOCUMENTS 4,419,514 12/1983 McKendry et al. ................ 546/346

Primary Examiner—Henry R. Jiles
Assistant Examiner—Robert C. Whittenbaugh

[57] ABSTRACT

There is disclosed a method for the conversion of a carboxylic acid group on the ring of an aromatic or N-heteroaromatic compound to a trichloromethyl group which comprises contacting the aromatic or N-heteroaromatic compound with a phenylphosphonous dichloride, phosphorus trichloride and chlorine.

6 Claims, No Drawings

METHOD FOR CONVERTING CARBOXYLIC ACID GROUPS TO TRICHLOROMETHYL GROUPS

FIELD OF THE INVENTION

The present invention relates to a method for the conversion of carboxylic acid groups to trichloromethyl groups.

BACKGROUND OF THE INVENTION

Direct chlorination of the methyl group on an aromatic or N-heteroaromatic compound presents problems when the compound contains other substituents such as alkoxy, alkyl or alkoxy or alkyl substituted aryl groups in addition to the methyl group to be chlorinated. In the above cases, direct chlorination of the methyl group would also result in chlorination of the substituent groups.

To solve the above problem, processes have been developed for obtaining a halogenated methyl group, particularly a trichloromethyl group, by treating a carboxylic acid group with phosphorus pentachloride, usually in the presence of excess thionyl chloride. Examples of these processes can be found at Chemical Abstracts 74, 125566y, Chemical Abstracts 79, 31986m and Chemical Abstracts 81, 105395h. The methods disclosed in the above references are specific for the conversion of a carboxylic acid group adjacent, or alpha, to the heteroatom of a N-heteroaromatic (N=nitrogen) compound.

A non-specific method for converting a carboxylic acid group to a trichloromethyl group is disclosed in U.S. Pat. No. 4,419,514. The method disclosed in the above patent uses a phenylphosphonic dichloride and phosphorus pentachloride. The above method suffers from the disadvantage of requiring the handling of solid phosphorus pentachloride which, due to its sensitivity to moisture, requires special handling conditions.

U.S. Pat. No. 4,249,009 discloses a process for the preparation of 2-chloro-5-trifluoromethylpyridine wherein 5-carboxy-2-hydroxypyridine is treated with a chlorinating agent and a fluorinating agent. The preferred chlorinating agent is phosphorus pentachloride and the inventors disclose that the reaction proceeds through an acid chloride intermediate. The above patent does not teach the formation of the trichloromethyl compound.

U.S. Pat. No. 4,167,525 discloses a process for the preparation of an aromatic acyl chloride. In the above patent, an aromatic carboxylic acid is first treated with phosphorus trichloride and chlorine. The phosphorus pentachloride by-product is treated with a reagent prepared from partially hydrolyzed phosphorus compounds to convert the phosphorus pentachloride to phosphorus oxychloride and the phosphorus oxychloride is removed by distillation. The above method suffers from the disadvantage of requiring additional phosphorus compounds to convert the phosphorus pentachloride to phosphorus oxychloride.

SUMMARY OF THE INVENTION

The present invention is directed to a method for the conversion of any carboxylic acid groups on an aromatic or N-heteroaromatic ring compound to trichloromethyl groups which comprises contacting an aromatic or N-heteroaromatic ring compound containing at least one carboxylic acid group with a phenylphosphonous dichloride, chlorine, and phosphorus trichloride.

DETAILED DESCRIPTION OF THE INVENTION

The present invention is directed to a method for the conversion of any carboxylic acid groups on an aromatic or N-heteroaromatic ring compound to trichloromethyl groups by reaction thereof with a phenylphosphonous dichloride, chlorine and phosphorous trichloride. This reaction can be characterized as follows:

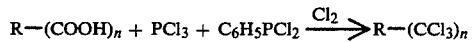

wherein R is an aromatic or N-heteroaromatic moiety and n is an integer from 1-2.

The aromatic or N-heteroaromatic carboxylic acid group containing compounds useful in the present invention can be any aromatic or N-heteroaromatic compound containing one or two carboxylic acid groups in non-sterically hindered ring positions and which compound is substantially chemically and physically stable under the acidic conditions of the reaction with the exception of the conversion of the carboxylic acid groups to the corresponding trichloromethyl groups. When there are two carboxylic acid groups present, they should be in non-adjacent ring positions to avoid steric hindrance problems.

The aromatic or N-heteroaromatic compounds can in addition be ring substituted with additional sterically compatible groups which are non-reactive under the conditions of the reaction such as chloro, fluoro, nitro, cyano, alkyl, alkoxy, alkylthio, aryl, alkyl-substituted aryl, alkoxy-substituted aryl, aryloxy, trichloromethyl or trifluoromethyl. To further insure that problems of steric hindrance be avoided, it is important that no groups having an atom radius larger than that of a chlorine atom be adjacent to a carboxylic acid group. In the case of aromatic compounds, it is necessary that a strong electron withdrawing group such as nitro or cyano also be present on the ring if the ring is substituted with an alkyl, alkylthio or alkoxy group. The above requirement is not necessary for N-heteroaromatic compounds.

In the present invention, the term "steric hindrance" is taken from the definition found in Hackh's *Chemical Dictionary*, Fourth Edition, McGraw-Hill Book Company, New York, page 638 (1969) which is as follows:

steric hindrance—The nonoccurence of an expected chemical reaction due to inhibition by a particular atomic grouping.

Thus, a sterically compatible group, as used throughout the present invention, designates a substituent group which would not interfere with the desired reaction because of steric hindrance.

In carrying out the process of the present invention, it is preferable that the aromatic or N-heteroaromatic compound, the phosphorus trichloride and the phenylphosphonous dichloride be added to the reaction vessel and then the chlorine added to the reaction mixture with vigorous stirring. It has also been found that best results are seen if the reaction vessel is not heated externally until approximately one half of the chlorine has been added.

After the reactants are all present, the mixture is heated at reflux: 100° C. to 175° C. The process is usually carried out at atmospheric pressure.

After the chlorine is added, said addition step ranging from about 1 to about 8 hours, the reaction is usually completed in from 4 to about 8 hours.

Upon completion of the reaction, the reaction mixture is cooled and pre-diluted with an appropriate solvent. Conventional washing and extraction procedures are then used to separate and recover the desired product.

It has also surprisingly been found that the process of the present invention can be carried out using less quantities of the phenylphosphonous dichloride to convert the carboxylic acid groups. In the process of the present invention, amounts ranging from about 0.1 to about 0.9 mole of the phenylphosphonous dichloride, based upon mole of the compound containing the carboxylic acid groups, can be used. If desired, quantities as high as 10 mole of the phenylphosphonous dichloride can be used, but usage of such large quantities would not be economical.

The amount of the chlorine employed in the present invention can range from about a 1:1 to about a 3:1 molar ratio of chlorine to PCl$_3$.

It will be appreciated by those skilled in the art to which this invention pertains that the total amount of phenylphosphonous dichloride and phosphorus trichloride used to convert the carboxylic acid group should be in an amount equal to or exceeding a 2:1 ratio of the total reactants per carboxylic acid group. Such a ratio insures the conversion of the two oxygens of the carboxylic acid groups.

In the present invention, the phenylphosphonous dichlorides which can be used include those corresponding to the formula

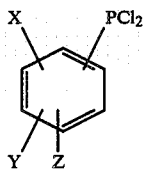

(I)

wherein X, Y and Z are the same or different and represent hydrogen, fluoro, chloro, cyano, trifluoromethyl, nitro and alkyl sulfonyl of from 1 to about 4 carbon atoms. Hereinafter, the term "phenylphosphonous dichloride" includes a phenylphosphonous dichloride substituted by any of the above groups.

The compounds produced by the processes of the present invention are useful for a variety of purposes. Trichloromethyl aromatic compounds are useful as agricultural intermediates. Trichloromethyl N-heteroaromatic compounds, such as 3-trichloromethyl pyridine, are useful intermediates for the production of agricultural chemicals, including both insecticides and pesticides.

The following Examples further illustrate the present invention.

EXAMPLE 1

This Example illustrates the conversion of nicotinic acid to 3-trichloromethyl pyridine using phenylphosphonous dichloride, phosphorus trichloride and chlorine.

To a 3 liter, 3-necked flask fitted with a thermometer, mechanical stirrer, chlorine inlet tube, and condenser were added 123 grams (1 mole) of nicotinic acid, 200 grams (1.1 moles) of phenylphosphonous dichloride and 164 grams (1.2 moles) of phosphorus trichloride. With vigorous stirring, chlorine was bubbled into the reaction mixture. After approximately half the chlorine had been added, the mixture was heated. Chlorine addition continued until approximately 220 grams (3 moles) of chlorine had been added. After all the chlorine had been added, (~4 hours) the mixture was heated at 130°–133° C. for an additional 4 hours.

At the conclusion of the reaction, 247 grams of the clear solution were worked up in the following manner. The solution was allowed to cool, was pre-diluted with 300 milliliters of methylene chloride, and was then poured into a 1 liter beaker containing ~800 milliliters of ice. The solution was then neutralized with 20% NaOH to pH 8, and the organic layer was separated and washed with 200 milliliters of methylene chloride. The organic layers were combined, dried over sodium sulfate and sodium carbonate and stripped on a rotary evaporator to yield 69.5 grams of a clear oil. The yield was 71%.

Gas liquid chromatography showed

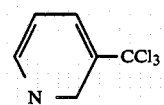

[COMPOUND A]

as the major peak (78% area) and

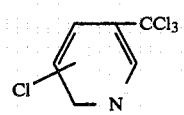

[COMPOUND B]

as the minor peak (7% area) with less than 10% solvent peak.

EXAMPLE 2

This Example shows that the quantity of phenylphosphonous dichloride used to convert the carboxylic acid group can be reduced to less than one mole.

To a 3 liter, 3-necked flask were added 62 grams (0.5 mole) of nicotinic acid, 137.5 grams (1 mole) of phosphorus trichloride and 45 grams (0.25 mole of phenylphosphonous dichloride. The mixture was stirred for 20 minutes at 40°–50° C. and 100 grams (1.4 mole) of chlorine was bubbled in over a period of ~7 hours. The by-product phosphorus oxychloride was distilled off at 100° C. under aspirator pressure. The remaining mixture was then diluted with 100 milliliters of methylene chloride and poured into 500 milliliters of ice. The solution was then neutralized with 25% NaOH, extracted three times with methylene chloride, dried over magnesium sulfate and stripped on a rotary evaporator. There was obtained 86 grams of product corresponding to an 88% yield. Gas liquid chromatography showed the major peak corresponding to the trichloromethyl pyridine.

Further features of the preferred and most preferred features of the present invention are found in the claims hereinafter.

What is claimed is:

1. A method for the conversion of a carboxylic acid group on the ring of an aromatic or N-heteroaromatic compound to a trichloromethyl group which comprises contacting at a temperature of from about 100° C. to about 250° C. the aromatic or N-heteroaromatic compound with (i) from about 0.5 to about 2.0 molar equivalents of phenylphosphonous dichloride per carboxylic acid group to be converted, (ii) phosphorus trichloride, and (iii) chlorine; wherein the molar ratio of chlorine to $PCl_3$ is from about 1:1 to about 3:1.

2. A method according to claim 1 wherein a carboxylic acid group on an aromatic compound is converted.

3. A method according to claim 1 wherein a carboxylic acid group on an N-heteroaromatic compound is converted.

4. A method according to claim 1 wherein the aromatic compound is ring substituted with at least one sterically compatible group chosen from the group consisting of chloro, fluoro, bromo, nitro, cyano, alkyl, alkoxy, alkylthio, hydroxy, aryl, alkyl substituted aryl, alkoxy substituted aryl, aryloxy or trifluoromethyl with the proviso that when the substituent is alkyl, alkylthio or alkoxy, a strong electron withdrawing group is present on the ring.

5. A method according to claim 1 wherein the N-heteroaromatic compound is ring substituted with at least one sterically compatible group from the group consisting of chloro, fluoro, bromo, nitro, cyano, alkyl, alkoxy, alkylthio, hydroxyl, aryl, alkyl substituted aryl, alkoxy substituted aryl, alkoxy substituted aryl, aryloxy or trifluoromethyl.

6. A method according to claim 1 wherein the compound produced is 3-trichloromethyl pyridine.

* * * * *